United States Patent
Sarma et al.

(10) Patent No.: US 8,521,294 B2
(45) Date of Patent: Aug. 27, 2013

(54) SYSTEM AND METHOD FOR DYNAMICALLY CONFIGURABLE DEEP BRAIN STIMULATION

(75) Inventors: Sridevi V. Sarma, McLean, VA (US); Emery N Brown, Brookine, MA (US); Emad Eskandar, Nahant, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/125,866

(22) PCT Filed: Oct. 26, 2009

(86) PCT No.: PCT/US2009/062072
§ 371 (c)(1),
(2), (4) Date: Sep. 19, 2011

(87) PCT Pub. No.: WO2010/048613
PCT Pub. Date: Apr. 29, 2010

(65) Prior Publication Data
US 2012/0016436 A1    Jan. 19, 2012

Related U.S. Application Data

(60) Provisional application No. 61/108,060, filed on Oct. 24, 2008.

(51) Int. Cl.
*A61N 1/36*      (2006.01)
*A61N 1/05*      (2006.01)
*A61N 1/08*      (2006.01)

(52) U.S. Cl.
USPC .......................................... 607/45

(58) Field of Classification Search
USPC .......................................... 607/45
See application file for complete search history.

(56) References Cited

U.S. PATENT DOCUMENTS

| | | | |
|---|---|---|---|
| 2007/0067003 A1* | 3/2007 | Sanchez et al. | 607/45 |
| 2007/0073355 A1* | 3/2007 | Dilorenzo | 607/45 |
| 2007/0100389 A1 | 5/2007 | Jaax et al. | |
| 2007/0150025 A1 | 6/2007 | DiLorenzo et al. | |
| 2007/0191704 A1* | 8/2007 | DeCharms | 600/411 |
| 2007/0203540 A1 | 8/2007 | Goetz et al. | |
| 2010/0023089 A1* | 1/2010 | DiLorenzo | 607/45 |

OTHER PUBLICATIONS

Bear et al. "Neuroscience: Exploring the Brain", 2006, Lippincott Williams & Wilkins, 3rd edition, p. 78.*
Truccolo et al. "A Point Process Framework for Relating Neural Spiking Activity to Spiking History, Neural Ensemble, and Extrinsic Covariate Effects." J Neurophysiol 93:1074-1089, 2005. First published Sep. 8, 2004.*
International Search Report and Written Opinion under date of May 12, 2010 in connection with PCT/US2009/062072.

* cited by examiner

*Primary Examiner* — Carl H Layno
*Assistant Examiner* — Erin Piateski
(74) *Attorney, Agent, or Firm* — Quarles & Brady, LLP

(57) ABSTRACT

A DBS system and method for predicting future neurological activity in a subject and administering a corrective electrical stimulation signal to prevent anticipated pathological neuronal activity. The DBS system includes an implantable electrode configured to both record neuronal activity from a target brain area in a subject and administer the corrective electric stimulation signal to the target area. The DBS system also includes a controller configured to determine the characteristics of the corrective electrical stimulation signal based on point process models of healthy and pathological neuronal activity in the target area.

18 Claims, 3 Drawing Sheets

SYSTEM AND METHOD FOR DYNAMICALLY CONFIGURABLE DEEP BRAIN STIMULATION

CROSS-REFERENCE TO RELATED APPLICATIONS

This application is based on, claims the benefit of, and incorporates herein by reference in their entirety, PCT International Application PCT/US2009/062072 filed on Oct. 26, 2009 and U.S. Provisional Patent Application Ser. No. 61/108,060 filed on Oct. 24, 2008, and entitled "SYSTEM AND METHOD FOR DYNAMICALLY CONFIGURABLE DEEP BRAIN STIMULATION."

BACKGROUND OF THE INVENTION

Neurodegenerative diseases plague a large number of individuals world wide. For example, an estimated 3-4 million people in the US have Parkinson's disease (PD), which is a chronic progressive neurodegenerative disease that occurs when dopaminergic neurons in the substantia nigra pars compacta of the midbrain degenerate, causing resting tremor, rigidity, and bradykinesia. Currently, there is no cure or definitive means to stop the progression of many neurodegenerative diseases and PD is just one example. However, medications and surgery can relieve many of the symptoms. Such treatments for PD have been developed based on an improved understanding of basal ganglia (BG) anatomy and physiology.

It has been long appreciated that PD follows the degeneration of dopaminergic neurons in the substantia nigra pars compacta. This triggers a cascade of functional changes in the BG that leads to abnormal activity in its output nuclei, the substantia nigra reticulata and globus pallidus internus. Therefore, the goal of traditional treatment is to enhance concentrations of dopamine, or to modify the activity of the output nuclei by creating lesions in target areas, or more recently by using deep brain stimulation (DBS).

DBS is a surgical procedure in which a stimulating probe is implanted in a targeted area, typically the subthalamic nucleus (STN), which is connected to an insulated wire that is passed under the skin of the head, neck, and shoulder and terminated at a neurostimulator, which typically sits inferior to the clavicle. At major surgical centers the surgery has become routine. Patient's motor symptoms generally decrease with treatment and they can regain quality of life and reduce their medications, which have serious side effects.

While traditional DBS is a valuable tool for treating neurological disorders, the stimulation signal must be optimized post-operatively. FIG. 1 provides schematic depiction of the "open loop" feedback system of traditional DBS systems, in which both natural external stimulus x(t) and an administered DBS signal u(t) affect the neuronal activity y(t) of a target region in a subject's brain. The neuronal activity y(t) in turn affects the behavior b(t) of the subject's body, which feeds back to affect the target region. The DBS system is not responsive to feedback from either y(t) or b(t). Therefore, identification of a stimulation signal u(t) that elicits an appropriate subject response is achieved by a manual calibration process in which a multitude of different stimulation signals are evaluated by trial-and-error. Manual calibration is costly in terms of medical resources and can limit the number of patients that a neurologist may treat simultaneously. Calibration can take several weeks or months, during which the high expectations of the subject having an implanted DBS system may not be met, thereby leading to subject depression and medication use. Moreover, current DBS waveforms are high-frequency and can leak into neighboring brain areas, causing side effects. Beyond such undesirable side effects, current DBS systems, employing high-frequency stimulation waveforms, consume significant amounts of power and rapidly drain batteries that must be replaced surgically.

It would therefore be desirable to have DBS system that would reduce the resources needed for calibration and operation and provide more immediate and effective treatment to the patient. Such a system would improve patient care, reduce medical costs, increase the number of patients that a neurologist may treat simultaneously, and improve the performance characteristics, for example, battery life, of the device.

SUMMARY OF THE INVENTION

The present invention overcomes the aforementioned drawbacks by providing a system and method for performing deep brain stimulation that is capable of dynamic and continuous self-calibration. The system for performing deep brain stimulation includes an implantable electrode configured to measure a physiological parameter of a subject and deliver an electrical stimulation signal to a target area in the subject. The DBS system also includes a neurostimulator having a memory device having stored thereon a healthy model characterizing healthy neuronal activity in the target area and a pathological model characterizing pathological neuronal activity in the target area. The neurostimulator also includes a controller in communication with the implantable electrode and the memory device and configured to analyze the measured physiological parameter using the healthy model and the pathological model to identify a corrective electrical stimulation signal that, when delivered by the implantable electrode to the target area, reduces pathological neuronal events in the target area.

The method for performing deep brain stimulation includes the steps of measuring a physiological parameter from a target area of a subject using an electrode implanted in the subject and analyzing the measured physiological parameter using a healthy model characterizing healthy neuronal activity in the target area and a pathological model characterizing pathological neuronal activity in the target area to identify a corrective electrical stimulation signal that, when delivered to the target area, reduces pathological neural events in the target area. The method further includes the step of administering the corrective electrical stimulation signal to the target area using the implanted electrode.

Various other features of the present invention will be made apparent from the following detailed description and the drawings.

DETAILED DESCRIPTION OF THE PREFERRED EMBODIMENT

Figure 2:
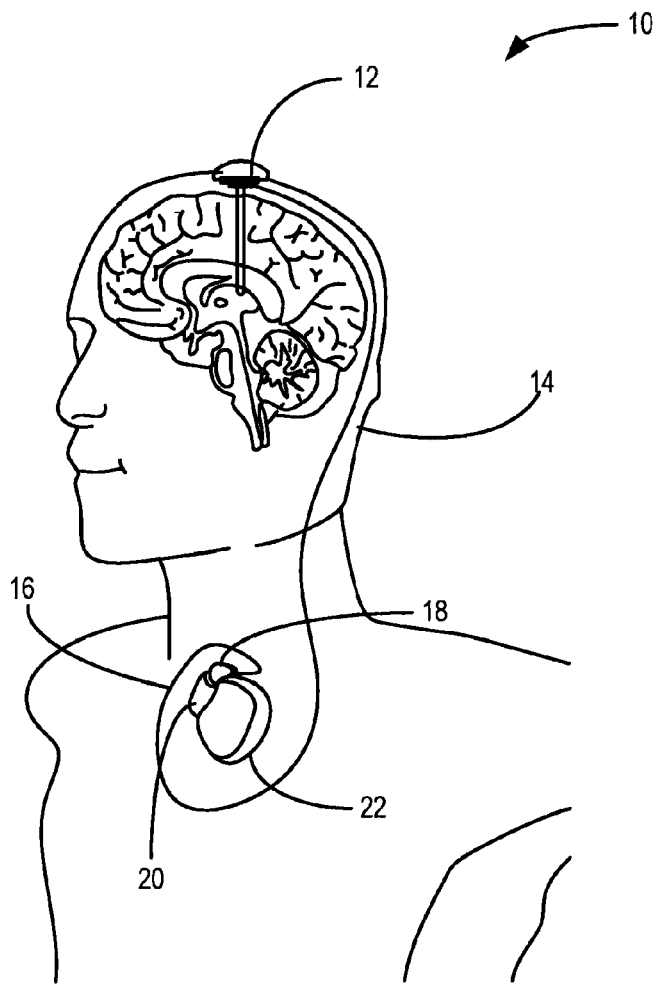
FIG. 2 is a schematic of a DBS apparatus in accordance with the present invention.

Referring to FIG. 2, the present invention provides a DBS system 10 capable of predicting future neural activity and administering electrical stimulation to a target brain area, such as the STN, to prevent anticipated pathological neural activity. The DBS system 10 includes an electrode probe 12 that is capable of both stimulating populations of neurons and measuring single-unit neuronal activity. The probe 12 is typically implanted in the target and connected via an insulated lead 14 to a neurostimulator 16. It is contemplated that the lead 14 runs under the skin of the head, neck, and shoulder and that the neurostimulator 16 is implanted to sit inferior to the clavicle. The neurostimulator 16 includes a pulse generator 18, a controller 20, and a battery pack 22 to power the DBS system 10. The neurostimulator 16 can also include a memory to store measured neural activity data and models for implementation on the controller 20.

In operation, the DBS system 10 acquires neuronal activity, or spike train, data with the electrode probe 12. This neuronal activity data is carried via lead 14 to the neurostimulator 16 where it is processed by the controller 20. The controller 20 analyzes the data and identifies a corrective stimulation signal that will prevent anticipated pathological neural events. The selected stimulation signal is then generated by the pulse generator 18 and delivered via the lead 14 to the electrode probe 12, which administers the stimulation signal to the target area. Depending on the predicted neural activity, the stimulation signal may inhibit neurons, excite neurons, or do nothing.

Figure 3:
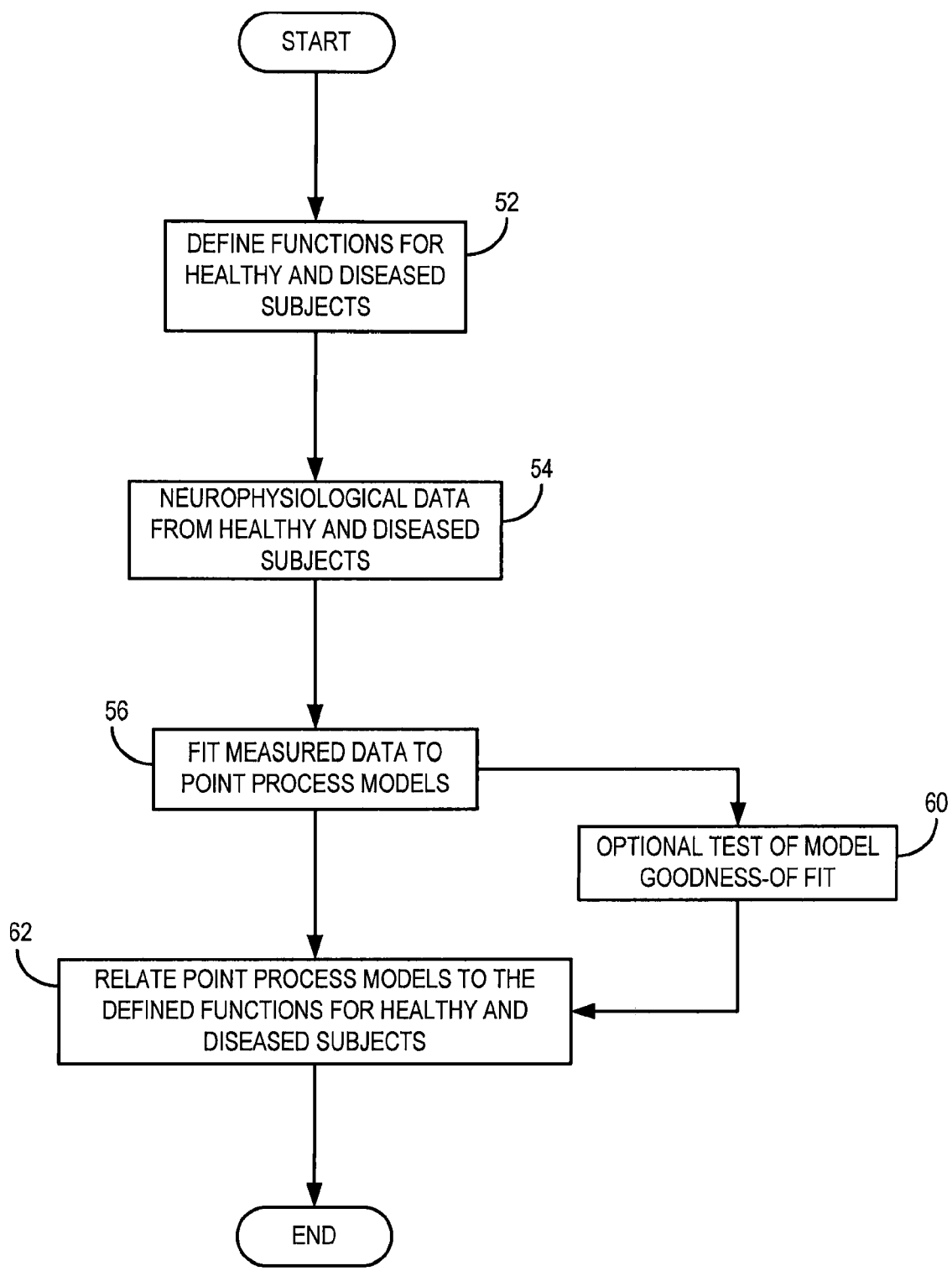
FIG. 3 is a flowchart setting forth the process used to create models for healthy and diseased subjects in accordance with the present invention.
Figure 4:
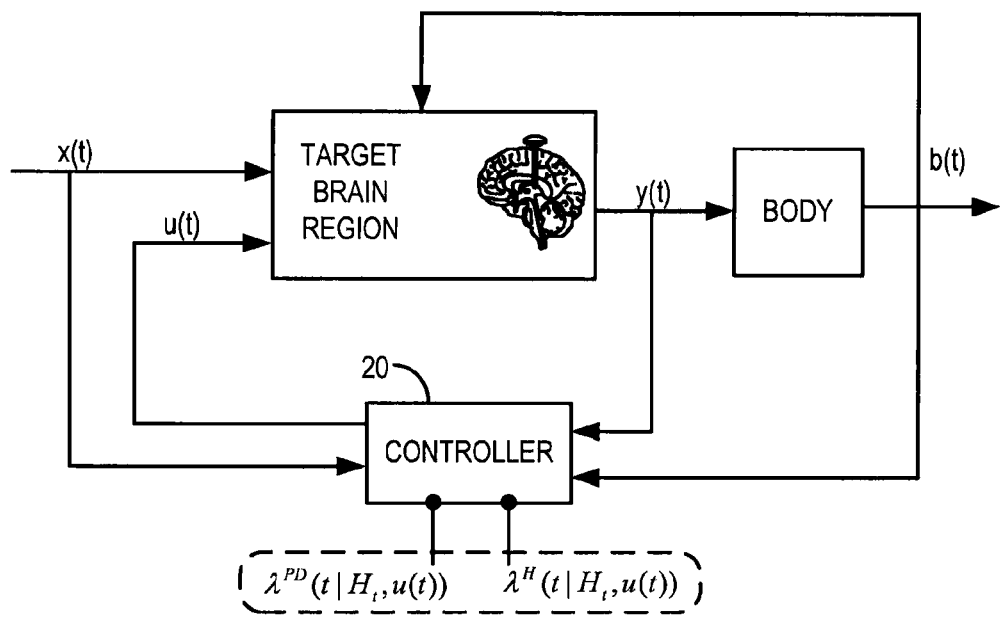
FIG. 4 is a block diagram of a DBS system in accordance with the present invention.

Referring now to FIGS. 3 and 4, to operate as described above, the controller 20 employs control algorithms based on models that characterize the neural activity of healthy and PD subjects. Typically, the models relate neural spike trains for both healthy and diseased subjects to natural extrinsic factors, such as the environment x(t) and behavioral stimuli b(t), and intrinsic dynamics, such as the history of neural spiking activity y(t) and local neural network activity. A method for constructing such models begins at process block 52, with the definition of functions characterizing neural spike trains in healthy and PD subjects. Specifically, a PD patient model y(t) and a healthy model $y^H(t)$ can be defined as follows:

$$y(t) = f^{PD}(t, X_t, Y_t, u(t)) \qquad \text{Eqn. 1;}$$

and $$y^H(t) = f^{PD}(t, X_t, B_y, Y_t^H) \qquad \text{Eqn. 2;}$$

where y(t) is the scalar value of the spike train (generally, either 0 or 1) at a given time t, x(t) is the value of natural extrinsic stimuli, and b(t) is the value of behavioral stimuli. $Y_t$, $Y^H_t$, $X_t$, and $B_t$ are the sequences of historical values over the time interval from 0 to t for y(t), $j^H(t)$, x(t) and b(t), respectively. The variables $Y_t$, $X_t$, and $B_t$ may be grouped into $H_t$, which therefore gives the history of spiking activity and its covariates up to time t. At process block 54, neurophysiological data for the construction of functions $f^{PD}$ and $f^H$ is acquired by recording neural activity from the same target brain area of both healthy and PD subjects that are executing the same behavioral task. For example, the neuronal activity of subjects having PD can collected in an operating room by functional neurosurgeons during the implantation of a DBS device, while healthy subject data can be collected from primates under similar experimental conditions.

At process block 56, the collected healthy and PD neural activity data are fit to models to provide a basis for estimating of y(t) and $y^H(t)$. This can be achieved using a point process paradigm that overcomes difficulties in characterizing neural activity dynamics, particularly those associated with noise and the dependence of neural activity on both intrinsic and extrinsic factors. A point process is a binary stochastic process defined in continuous time, for example, the number of neuronal spikes in a given time interval, and is characterized entirely by a conditional intensity function (CIF). A CIF for a point process model relating the spiking propensity of target brain area neurons to factors associated with environmental conditions, behavioral stimuli, and the neurons' spiking history can be defined as follows:

$$\lambda(t \mid H_t, u(t)) = \lim_{\Delta \to 0} \frac{Pr(N(t+\Delta) - N(t) = 1 \mid H_t, u(t))}{\Delta}; \qquad \text{Eqn. 3}$$

where N(t) is the number of spikes in a time interval [0,t] for t∈(0,T] and $t_1$ to $t_n$ denotes the time of measured neuronal spikes such that $0 < t_1 < t_2 < \ldots < t_n \leq T$. Multivariate point process models may also be employed in accordance with the present invention, for example, $\lambda(t|H_t, u(t))$ and N(t) may be vector-valued when modeling several neurons. Accordingly, Eqn. 3 defines the probability of a spike in each neuron in any small time interval (t,t+Δ) as follows:

$$Pr(\text{spike in}(t,t+\Delta)|H_t) \approx \lambda(t|H_t)\Delta \qquad \text{Eqn. 4.}$$

Thus, when Δ is small, Eqn. 4 is approximately equal to the spiking propensity at time t. While the model can be fitted to measured neuronal activity data using any appropriate parametric or nonparametric modeling class, it is contemplated that the present invention employs a generalized linear model (GLM) framework. In a GLM, the log of the CIF is a linear function of model parameters. A GLM is advantageous because it separates the contributions of extrinsic and intrinsic factors to the probability that the neuron will spike at a given time t. A GLM also provides an efficient computational scheme for estimating model parameter and a likelihood framework for conducting statistical inferences based on the estimated model. For example, a GLM framework for fitting collect neuronal activity data to the above CIF employ the following relations:

$$\lambda(t \mid H_t, u(t), \theta) = \theta_0 + \sum_{i=1}^{I} \alpha_i f_i(\text{extrinsic covariates, } t) + \sum_{j=1}^{J} \beta_j g_j(\text{intrinsic covariates, } t); \qquad \text{Eqn. 5}$$

where the vector $\theta_0 = \{\alpha, \beta, \gamma\}$ denotes the unknown parameters, such as spike times, to be estimated from the collected data. In this equation, the logarithm of the CIF is linear for $\theta_0$ and $f_i$ and $g_j$ are basis functions and may be any arbitrary nonlinear function. It should be noted that this GLM is an extension of a multiple linear regression model in which the spike times being estimated need not be Gaussian.

At process block 60, the goodness-of-fit of the point process model can optionally be tested. This can be achieved by generating a Kolmogorov-Smirov (KS) plot that compares the empirical cumulative distribution function of time-scaled spike times to the cumulative distribution function of a unit rate exponential. Improved goodness-of-fit is indicated if the KS plot lies on the 45 degree line. Further, a 95 percent confidence bounds can be computed for the degree of agreement using the distribution of the KS statistic. To test the independence of rescaled times, the spike times can be transformed into Gaussian rescaled times with zero means and unit variances. Since lack of correlation is equivalent to independence for Gaussian random variables, the autocorrelation function (ACF) of the Gaussian rescaled times can be plotted and the number of points of the ACF lying outside the 95% confidence intervals can be counted.

At process block 62, the point process models can be related back to the functions $y^H(t)$ and $y(t)$. Using time units of msecs and assuming $\Delta=1$, this can be by noting that at any time t, $f^{PD}$ and $f^H$ are random variables that take on the values 0 or 1 according to the following probabilities:

$$\text{Prob}[f^{PD}(t,H_t,u(t))=1] \approx \lambda^{PD}(t|H_t,u(t)) \quad \text{Eqn. 6;}$$

and $$\text{Prob}[f^H(t,H_t,u(t))=1] \approx \lambda^H(t|H_t) \quad \text{Eqn. 7.}$$

Initial point process models characterizing healthy and PD STN neuronal activity in the absence of DBS stimulation, that is, $\lambda^{PD}(t|H_t)$ and $\lambda^H(t|H_t)$, can be generated from neuronal activity recordings from PD subjects and healthy primates by assuming u(t)=0. The primates are used as surrogates for healthy humans and the studies are performed under identical conditions, for example, as the PD subjects and primates perform the same task. Studies using such models can quantify prevalent abnormalities in PD activity not present in healthy activity. In particular, the neural activity of PD subjects exhibits 10-30 Hz oscillations, bursting, and persistent directional tuning, all of which may directly related to the well-known PD motor symptoms of resting tremor, bradykinesia, and rigidity. However, for the control algorithm used in the DBS system 10 of FIG. 2, it is beneficial to have a predictive model that characterizes the effect of different DBS inputs on spiking activity.

The model $\lambda^{PD}(t|H_t,u(t))$ can be predicted from $\lambda^{PD}(t|H_t)$ by making the following assumptions: First, the DBS signal u(t) is a sequence of the values 0, 1, −1, that is, the DBS signal is an aperiodic train of positive and negative pulses, where a value of 1 indicates a pulse with positive height and a value of −1 indicates a pulse with negative height. Specifically, the DBS signal is a time sequence of independent distributed random variable with the following probability distributions:

$$Pr(u(t)=1)=p(t) \quad \text{Eqn. 8;}$$

$$Pr(u(t)=0)=q(t) \quad \text{Eqn. 9;}$$

and $$Pr(u(t)=-1)=1-(q(t)+p(t)) \quad \text{Eqn. 10.}$$

Secondly, when the DBS signal u(t) is applied, it adds to the neuronal spike train of each STN neuron it impacts. If the spike train of a single neuron can be denoted as y(t) with a CIF $\lambda^{PD}(t|H_t)$, then this addition obeys the following rules:
  a. If for a given time t, y(t)=0 and u(t)=1, then y(t)+u(t)=1 (event A)
  b. If for a given time t, y(t)=0 and u(t)=0, then y(t)+u(t)=0
  c. If for a given time t, y(t)=0 and u(t)=−1, then y(t)+u(t)=0
  d. If for a given time t, y(t)=1 and u(t)=1, then y(t)+u(t)=1 (event A)
  e. If for a given time t, y(t)=1 and u(t)=0, then y(t)+u(t)=1 (event A)
  f. If for a given time t, y(t)=1 and u(t)=−1, then y(t)+u(t)=0

Lastly, the new spiking activity z(t)=y(t)+u(t) is a binary sequence of 0's and 1's and is point process with the following CIF:

$$\lambda^z(t|H_t) = P(z(t)=1|H_t) \equiv \lambda^{PD}(t|H_t,u(t)) \quad \text{Eqn. 11}$$
$$= P(\text{event } a|H_t)$$
$$= p(t)(1-\lambda^{PD}(t|H_t)) + p(t)\lambda^{PD}(t|H_t) + q(t)\lambda^{PD}(t|H_t)$$
$$= p(t) + q(t)\lambda^{PD}(t|H_t);$$

where $H_t$ is the history of y(t) and any other extrinsic factors up to time t, that is $H_t = \{X_t, B_t, Y_t\}$.

Figure 1:
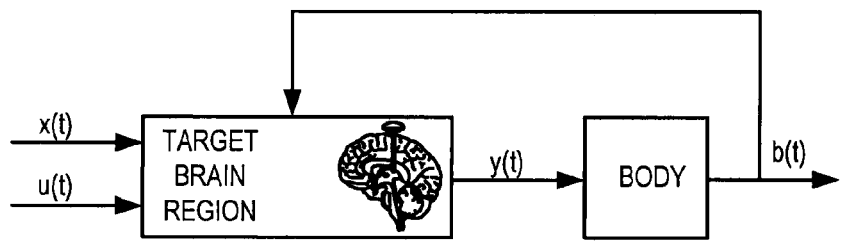
FIG. 1 is a block diagram depicting a prior-art DBS system.

Referring now to FIGS. 2 and 4, healthy and PD spike train models generated using the above method can serve as the basis for controller algorithms that predict future neuronal activity based on measured factors and determined a corrective electrical stimulation signals to correct for anticipated pathological neuronal activity. As shown schematically in FIG. 4, the controller 20 may use such a model as a basis for 1) estimating environmental factors and behavioral stimuli from spike train measurements, 2) determining in real-time the DBS stimulation signal that minimizes a difference between a PD subject's spike train and the predicted spike train of a healthy subject, and 3) translating this information into continuous voltage signal to be generated by the pulse generator 18 and delivered to the target brain area by the electrode 12. In contrast to traditional DBS systems, such as that depicted of FIG. 1, the present invention can be considered as a "closed loop" system, since controller determines the corrective stimulation signal u(t) based on environmental and behavioral stimuli, x(t) and b(t), respectively, as well as the neural activity of the target region y(t).

The environment and behavioral stimuli can be estimated from neuronal data acquired by the electrode 12 by maximizing the following a posteriori probability:

$$Pr(\text{stimuli}|\text{neuronal spiking activity up to time } t) \quad \text{Eqn. 12;}$$

though it should be noted that this process may be skipped if the CIF is not a function of unknown environment and behavioral stimuli. The real-time determination of the DBS stimulation signal can be achieved by optimizing a distance function. The high-level control objective of the present invention is to match the neural activity of a PD subject in which the DBS system 10 of FIG. 2 is implanted to that of a healthy representative. With the point-process paradigm, this translates to matching the CIF of the PD subject with that of a healthy subject. This match between the two CIFs can be achieved by minimizing the following distance relationship:

$$\text{distance}\{\lambda^{PD}(t|H_t,u(t)), \lambda^{Healthy}(t|H_t)\} \quad \text{Eqn. 13.}$$

Figure 5:
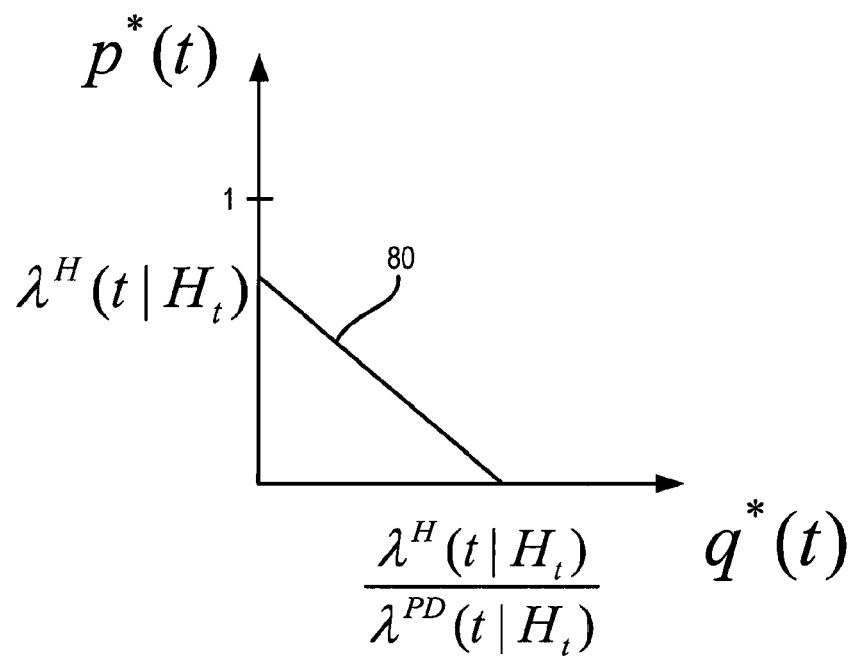
FIG. 5 is graph showing a segment of optimal solutions for p*(t) and q*(t) in accordance with the present invention.

Referring to FIG. 5, it should be noted that the distance can be expressed using any relevant function. For example, the distance function may be selected to equate the average of each spike train in the least-squares sense by setting the distance as the expected value of the square difference of the PD spike train with DBS input (z(t)=y(t)+u(t)) and a healthy spike train h(t) as follows:

$$\text{distance}\{\lambda^{PD}(t|H_t,u(t)), \lambda^H(t|H_t)\} = E\{[z(t)-h(t)|H_t]^2\}. \quad \text{Eqn. 14}$$

Thus, the solution to the least-squares problem:

$$\min_{u(t)}(E\{[z(t)-h(t)\mid H_t]^2\}) = \min_{u(t)}(E\{[y(t)+u(t)-h(t)\mid H_t]^2\}); \quad \text{Eqn. 15}$$

is given by:

$$\begin{aligned} E\{z(t)\} &= E\{y(t)\} + E\{u^*(t)\} \\ &= E\{h(t)\} \Rightarrow \lambda^{PD}(t\mid H_t, u^*(t)) \\ &= \lambda^H(t\mid H_t) = p^*(t) + q^*(t)\lambda^{PD}(t\mid H_t); \end{aligned} \quad \text{Eqn. 16}$$

where p*(t), q*(t), and u*(t) denote optimal values for p(t), q(t), and u(t). It should thus be noted that there are infinitely many optimal solutions for p*(t), q*(t) that define the stochastic properties of u*(t). Specifically, the set of all possible optimal solutions lie on the line segment 80 of FIG. 5. This line segment moves up and down with a slope of −1 as the values of $\lambda^H(t|H_t)$ and $\lambda^{PD}(t|H_t)$ change over time, with the constraint that $\lambda^H(t|H_t)$ and $\lambda^{PD}(t|H_t)$ are always between 0 and 1. If, for example, $\lambda^H(t|H_t)$ is close to zero and $\lambda^{PD}(t|H_t)$ is close to one, then both p*(t) and q*(t) are close to zero, which implies that u*(t)=−1 with a probability close to 1. Thus, the healthy spike train $y^H(t)$ and PD spike train y(t) will respectively be 0 and 1 with high probability and the DBS signal should inhibit y(t) so that z(t)=y(t)+u(t)=0.

The distance function can alternatively be dependent on the actual behavior of the PD subject in which the DBS system 10 of FIG. 2 is implanted. Instead of matching the neural activity patterns of the subject to those of a healthy reprehensive, the distance between the motor behavior, for example, movement time, movement velocity, or tremor frequency resulting from the motor behavior, of a healthy and the PD subject can be minimized. For example, this can be achieved by minimizing the following relationship:

$$\text{distance}\{\lambda^{PD}(t|H_p u(t)), \lambda^H(t|H_t)\} = E\{[V(t)^{PD} - V(t)^H]^2\} \quad \text{Eqn. 17};$$

where V(t), for example, is the movement velocity as a function of time. Since V(t) is a function of neural activity, a model of the body, as depicted in FIG. 4, should be estimated either from measured data or biophysical laws. Further, though single input-output models for PD subject STN activity are described above, other input-output point process models with CIFs $\lambda^H(t|H_t,u(t))$ can be selected and subjected to similar optimization procedures.

Referring again to FIG. 2, regardless of the distance function used, the information provided by the controller 20 following minimization can be translated by the pulse generator 18 into a continuous voltage capable of eliciting an appropriate neural activity from the PD subject. As described above, the corrective stimulation signal can take on one of three possible pulse height values, {−1, 0, 1}, at any given time bin. Therefore, a value of u(t)=−1 indicates that the pulse generator 18 should produce an electrical signal that inhibits a target neuron, while a value of u(t)=1 indicates that the pulse generator 18 should produce an electrical signal that excites the target neuron. Likewise, a value of u(t)=0 indicates that the pulse generator 18 should do nothing.

Because the present invention administers a stimulation signal to the subject based on observed and predicted physiological parameters of a PD subject rather than a stimulation pattern set by a physician, it can be considered as a "self-calibrating" device. Accordingly, the present can test subject response to a broad set of stimulation signal waveforms and, based on their observed effect, develop waveforms that provide improved patient response and device performance. For example, the present invention could automatically develop a stimulation signal for a particular subject using stimulation signal frequencies lower that those used by traditional DBS devices. This is advantageous, since a lower frequency stimulation signals offers reduced power consumption, thereby prolonging device battery life, and reduced patient side effects by substantially limiting the leakage of stimulation signal to brain areas surrounding the target area. Repeatedly adjusting the stimulation signal to this degree would be prohibitively time-consuming if done using tradition, that is, manual, calibration techniques.

The present invention has been described in terms of the various aspects and features, and it should be appreciated that many equivalents, alternatives, variations, and modifications, aside from those expressly stated, are possible and within the scope of the invention. Therefore, the invention should not be limited to a particular described embodiment.

The invention claimed is:

1. A system for performing deep brain stimulation, the system comprising:
   an implantable electrode configured to measure a physiological parameter of a subject and deliver an electrical stimulation signal to a target area in the subject;
   a neurostimulator including:
   a memory device having stored thereon a healthy model characterizing healthy neuronal activity in the target area and a pathological model characterizing pathological neuronal activity in the target area;
   a controller in communication with the implantable electrode and the memory device and configured to analyze the measured physiological parameter using the healthy model and the pathological model to identify a corrective electrical stimulation signal that, when delivered by the implantable electrode to the target area, reduces pathological neuronal events in the target area,
   wherein the controller is further configured to identify the corrective electrical stimulation signal by minimizing a difference between:
   predicted pathological neuronal activity determined as an output of the pathological model using the measured physiological parameter as an input, and
   predicted healthy neuronal activity determined as an output of the healthy model using the measured physiological parameter as an input.

2. The system as recited in claim 1 wherein the target area is the subject's subthalamic nucleus (STN) and the pathological neuronal activity is neuronal activity associated with Parkinson's disease and wherein the physiological parameter is single-unit neuronal activity in the subject's STN.

3. The system as recited in claim 1 wherein the corrective electrical stimulation signal causes one of neuronal inhibition in the target area and neuronal excitation in the target area.

4. The system as recited in claim 1 wherein the neurostimulator further includes a battery pack configured to power the neurostimulator and a pulse generator configured to generate the corrective electrical stimulation signal under the direction of the controller.

5. The system as recited in claim 1 further comprising an insulated lead coupling the electrode to the neurostimulator.

6. The system as recited in claim 1 wherein minimizing the difference between the predicted pathological neuronal activity and the predicted healthy neuronal activity includes employing the relationship:

$$\text{distance}\{\lambda^{PD}(t|H_p u(t)), \lambda^H(t|H_t)\},$$

in which $\lambda^{PD}(t|H_t, u(t))$ is a conditional intensity function for the pathological model and $\lambda^H(t|H_t)$ is a conditional intensity function for the healthy model, wherein $H_t$ denotes a history of neuronal activity preceding time t and u(t) denotes the corrective electrical stimulation signal.

7. The system as recited in claim 6 wherein the pathological model and healthy models are point process models constructed by acquiring pathological neuronal activity data and healthy neuronal activity data from a pathological subject and healthy subject, respectively, and wherein fitting the measured pathological and healthy neuronal activity data to the point process models is done using a generalized linear model technique.

8. The system as recited in claim 7 wherein the point process models are based on functions defining healthy neuronal activity and pathological neuronal activity in the target area of the subject.

9. The system as recited in claim 8 wherein the function defining healthy neuronal activity is a function of a healthy neuronal spike train at a given time, natural extrinsic stimuli, behavioral stimuli, and sequences of historical values thereof.

10. The system as recited in claim 8 wherein the function defining pathological neuronal activity is a function of a pathological neuronal spike train at a given time, natural extrinsic stimuli, behavioral stimuli, sequences of historical values thereof, and the corrective electrical stimulation signal.

11. The system as recited in claim 1 wherein the controller identifies the corrective electrical stimulation signal by minimizing a difference between a predicted pathological motor behavior determined by analyzing the measured physiological parameter with the pathological model and a predicted healthy motor behavior determined by analyzing the measured physiological parameter with the healthy model.

12. A method for performing deep brain stimulation, the method comprising:
a) measuring a physiological parameter from a target area of a subject using an electrode implanted in the subject;
b) analyzing the measured physiological parameter using a healthy model characterizing healthy neuronal activity in the target area and a pathological model characterizing pathological neuronal activity in the target area to identify a corrective electrical stimulation signal that, when delivered to the target area, reduces pathological neural events in the target area, wherein identifying the corrective electrical stimulation signal includes minimizing a difference between:
predicted pathological neuronal activity determined as an output of the pathological model using the measured physiological parameter as an input, and
predicted healthy neuronal activity determined as an output of the healthy model using the measured physiological parameter as an input; and
c) administering the corrective electrical stimulation signal to the target area using the implanted electrode.

13. The method as recited in claim 12 wherein administering the corrective electrical stimulation signal causes at least one of neuronal inhibition in the target area, neuronal excitation in the target area, and no induced change to neuronal activity in the target area.

14. The method as recited in claim 12 wherein minimizing the difference between the predicted pathological neuronal activity and the predicted healthy neuronal activity includes employing the relationship:

$$\text{distance}\{\lambda^{PD}(t|H_t, u(t)), \lambda^H(t|H_t)\},$$

in which $\lambda^{PD}(t|H, u(t))$ is a conditional intensity function for the pathological model and $\lambda^H(t|H_t)$ is a conditional intensity function for the healthy model, wherein $H_t$ denotes a history of spiking activity preceding time t and u(t) denotes the corrective electrical stimulation signal.

15. The method as recited in claim 14 wherein the pathological model and healthy models are point process models constructed by acquiring pathological neuronal activity data and healthy neuronal activity data from a pathological subject and healthy subject, respectively, and wherein fitting the measured pathological and healthy neuronal activity data to the point process models includes employing a generalized linear model technique, and wherein the point process models are based on functions defining healthy neuronal activity and pathological neuronal activity in the target area of the subject.

16. The method as recited in claim 15 wherein the function defining healthy neuronal activity is a function of a scalar value of a healthy neuronal spike train at a given time, natural extrinsic stimuli, behavioral stimuli, and sequences of historical values thereof.

17. The method as recited in claim 15 wherein the function defining pathological neuronal activity is a function of a pathological neuronal spike train at a given time, natural extrinsic stimuli, behavioral stimuli, sequences of historical values thereof, and the corrective electrical stimulation signal.

18. The method as recited in claim 12 wherein step b) includes minimizing a difference between a predicted pathological motor behavior determined by analyzing the measured physiological parameter with the pathological model and a predicted healthy motor behavior determined by analyzing the measured physiological parameter with the healthy model.

* * * * *

UNITED STATES PATENT AND TRADEMARK OFFICE
CERTIFICATE OF CORRECTION

| | |
|---|---|
| PATENT NO. | : 8,521,294 B2 |
| APPLICATION NO. | : 13/125866 |
| DATED | : August 27, 2013 |
| INVENTOR(S) | : Sridevi V. Sarma, Emery N. Brown and Emad Eskandar |

Page 1 of 1

It is certified that error appears in the above-identified patent and that said Letters Patent is hereby corrected as shown below:

In the Specifications

Column 1, lines 13-14

Please insert the following after the CROSS-REFERENCE TO RELATED APPLICATIONS paragraph and before the BACKGROUND OF THE INVENTION title:

-- STATEMENT REGARDING FEDERALLY SPONSORED RESEARCH
This invention was made with Government support under Grant No(s). NS041851 and EY017658 awarded by the National Institutes of Health. The Government has certain rights in this invention. --

Signed and Sealed this
Twenty-second Day of April, 2014

Michelle K. Lee
*Deputy Director of the United States Patent and Trademark Office*